United States Patent [19]

Scott

[11] Patent Number: 4,881,528

[45] Date of Patent: Nov. 21, 1989

[54] SPINAL TRACTION AND SUPPORT UNIT USED WHILE SEATED

[76] Inventor: Henry Scott, 1109 Rock Creek Dr., Wyncote, Pa. 19095

[21] Appl. No.: 260,755

[22] Filed: Oct. 21, 1988

[51] Int. Cl.⁴ ........ A61F 5/04

[52] U.S. Cl. ........ 128/75; 128/78

[58] Field of Search ........ 128/75, 71, 78

[56] References Cited

U.S. PATENT DOCUMENTS

| | | | |
|---|---|---|---|
| 2,984,238 | 5/1961 | Antell et al. | 128/75 |
| 3,167,068 | 1/1965 | Carr | 128/72 |
| 3,176,684 | 4/1965 | Walsh | 128/75 |
| 3,420,230 | 1/1969 | Ballard | 128/75 |
| 3,568,670 | 3/1971 | Gaylord, Jr. | 128/78 |
| 3,889,664 | 6/1975 | Heuser et al. | 128/75 |
| 4,030,489 | 6/1977 | Buckner | 128/75 |
| 4,583,533 | 4/1986 | Goodley et al. | 128/75 |
| 4,658,807 | 4/1987 | Swam | 128/78 |
| 4,715,362 | 12/1987 | Scott | 128/75 |
| 4,716,918 | 1/1988 | Hayashida et al. | 135/102 |
| 4,747,399 | 5/1988 | Glomstead | 128/75 |

FOREIGN PATENT DOCUMENTS

| | | | |
|---|---|---|---|
| 1509344 | 1/1967 | France | 128/75 |

*Primary Examiner*—William Pieprz
*Assistant Examiner*—Tonya Lamb
*Attorney, Agent, or Firm*—Millen, White & Zelano

[57] ABSTRACT

A sedentary traction and support unit for supporting the lumbosacral spine comprises a girdle with a U-shaped frame secured thereto. The girdle is secured about the patient's torso while the U-shaped frame extends below the girdle and engages the top surface of a seat. This permits the lower body weight to create traction. The unit provides relief to patients while they are sitting either on a chair, or the like, or on a vehicle seat.

7 Claims, 1 Drawing Sheet

SPINAL TRACTION AND SUPPORT UNIT USED WHILE SEATED

BACKGROUND OF THE INVENTION

The instant invention relates to lumbosacral traction systems. More particularly, the instant invention relates to a sedentary lumbosacral traction system which is used by a patient while sitting.

Presently known systems for providing traction or otherwise removing or minimizing compressive forces on the vertebral "discs" or other cartilage or bone structure in the lumbosacral pelvic region have the disadvantage that they require that patient to be hospitalized or at least confined to bed or to some complicated and/or otherwise restrictive device that does not allow the patient sufficient freedom to perform productive functions or other normal activities. Consequently, the recovery period is a tedious and an unproductive one, and the patient is often tempted to prematurely return to normal activities before recovery is complete. The unfortunate result is that the injured portions of the patients spine are usually unduly strained and the patient is again required to undergo traction which requires that the patient be hospitalized or remain in bed.

This inventor has recognized this problem and provides a solution in U.S. Pat. No. 4,715,362 which is directed to an ambulatory lumbosacral traction system. However, many patients spend most of their days seated and need a device which will provide relief while the patient is seated. When a patient is seated the weight of his or her upper body presses down on the lower back which can cause stress and pain if this area is injured or weak. In some instances, driving a vehicle can cause considerable discomfort in that the lower back is constantly subjected to impacts as the vehicle rolls over even small bumps.

Most prior art back supports utilize struts to transfer weight from a patient's upper body to the patient's pelvis. Exemplary of these devices is applicant's own U.S. Pat. No. 4,715,362. U.S. Pat. No. 3,167,068 discloses a traction system which the patient uses while sitting, however, in this traction system the patient is in effect suspended between a pair of posts mounted on a chair. Patients cannot get up and walk around when they desire simply because they are attached to the traction system by cables.

Accordingly, there is a need for a traction and support device which is especially useful to a patient who spends a great deal of time sitting and allow the patient ready mobility.

SUMMARY OF THE INVENTION

It is an object of the invention to provide a new and improved traction and support device for the lumbosacral spine which a patient utilizes while sitting.

With this object and other objects in mind, the instant invention contemplates a sedentary traction system which includes an elastic girdle which fits around the patients midsection just below the scapulae. Preferably, the elastic girdle is fastened in the front and is adjustable. The girdle has a pair of pockets adjacent the top end of the back in which are received the ends of a frame. The frame extends down past the girdle to a position where it can engage the top surface of the seat on which the patient sits.

In accordance with the preferred embodiment of the invention, the frame is vertically adjustable to accommodate patients of different heights and body configurations.

DESCRIPTION OF THE PREFERRED EMBODIMENT

Figure 3:
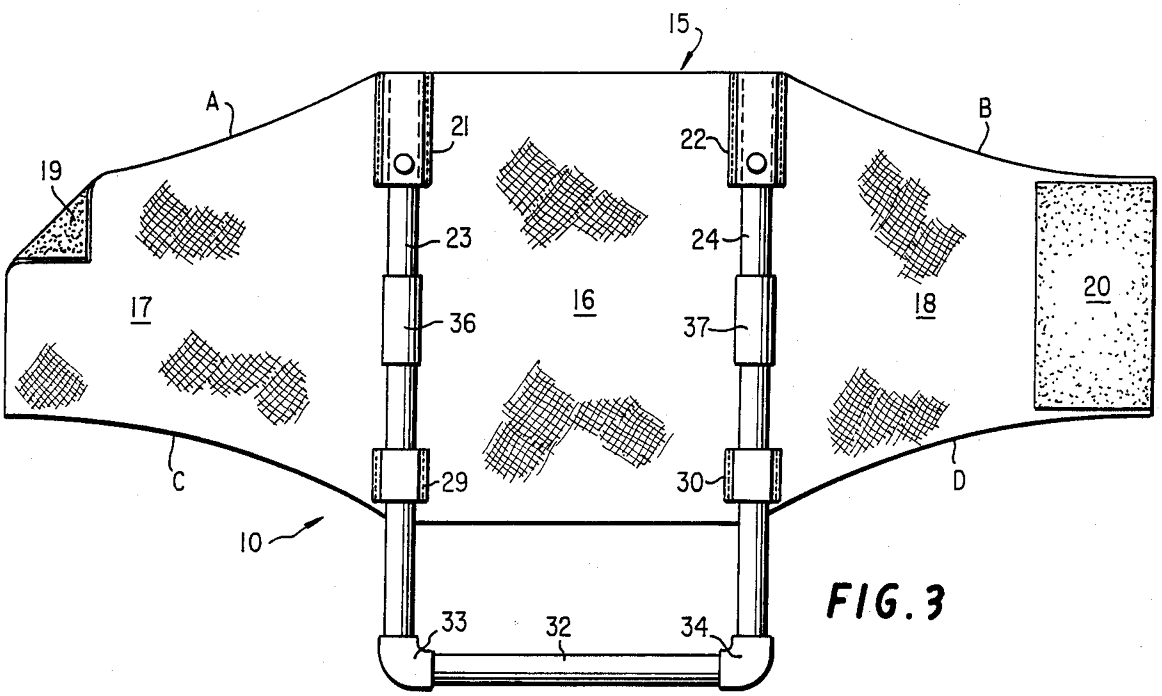
FIG. 3 is a planar view showing the traction and support unit of the instant invention laid out prior to use.
Figure 1:
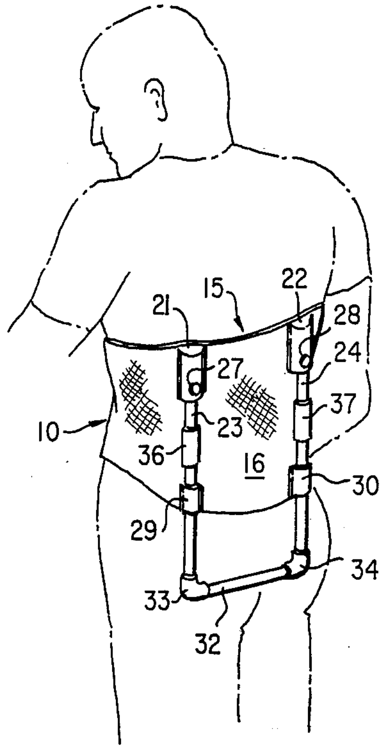
FIG. 1 is a perspective view of the device shown in FIG. 1 being worn by a patient.
Figure 2:
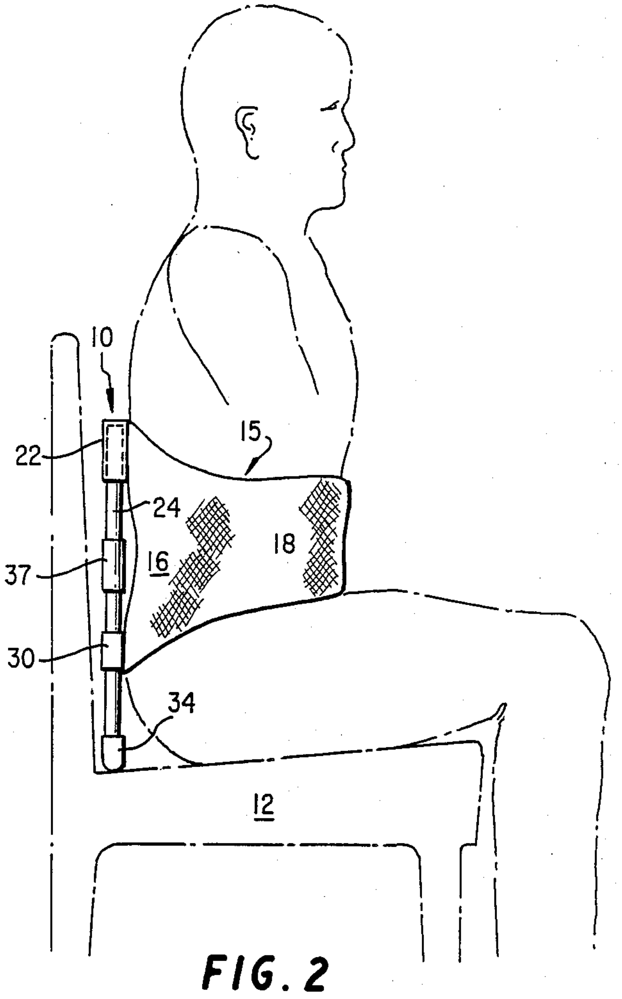
FIG. 2 is a side view of the device of FIGS. 1 and 2 being worn by the patient.

Referring now to FIGS. 1 and 2, a patient is shown wearing a traction and support unit, designated generally by the numeral 10, for providing support to the lumbosacral spine of the patient. The traction unit 10 is specifically designed to transfer support of the upper body from the patient's spine directly to a seat 12 on which the patient is sitting. The seat 12 can be any conventional chair in an office or at home or can be an automobile or truck seat. Many people with back problems spend a considerable amount of time sitting and sitting can aggravate back problems, as well as further injure already damaged spines.

The traction unit 10 comprises a girdle 15 made of a relatively thick padding material, preferably of latex or the like, so as to provide a degree of stiffness to the patient's torso when wrapped therearound. The girdle 15 has a rear panel portion 16 and a pair of front or wrapping panel portions 17 and 18. The front panel portion 17 has fixed thereto a pad of VELCRO hooks 19 which engage a pad of VELCRO loops 20 on the front panel portion 18 so as to secure the girdle 15 when the girdle is wrapped around the patients torso. The front panel portions 17 and 18 have upper edges A and B, respectively, and lower edges C and D, respectively, which converge toward one another so as to press on the patient's abdomen, as is seen in FIG. 2.

The girdle 15 has first and second pockets 21 and 22 adjacent the upper edge thereof. The pocket 21 receives therein a first vertical strut 23 while the pocket 22 receives therein a second vertical strut 24. Preferably the struts 23 and 24 are fixed within the pockets by screws or rivets 27 and 28 or by any suitable means. Loops of material 29 and 30 which are fixed to the rear panel 16 of the girdle 15 and receive the ververtical struts 23 and 24 respectively therethrough to stabilize the struts with respect to the girdle. Preferably, the sleeves 29 and 30 tightly retain the struts so that struts cannot slide with respect to the girdle 15. Extending across the lower ends of the vertical struts 23 and 24 is a base strut 32 which is fixed to the struts by elbows 33 and 34, or the like. The base strut 32 rests on the top surface of the seat 12 and helps keep the struts in position to form a U-shaped frame which cooperates with the girdle 15 to provide a stable traction device wherein a substantial portion of the weight of the patient's upper body is assumed by the frame. Also, this permits the lower body's weight to create traction.

In order to accommodate patients of different heights and body configurations, the vertical struts 23 and 24 may be axially adjustable by configurating the struts in telescopic sections with tightening sleeves 36 and 37 for locking the vertical struts at a selected length. Further, adjustment can be made by elevating or lower the entire girdle.

The traction and support unit 10 provides relief for sedentary patients enabling them to perform desk work and to drive vehicles with increased comfort, which activities they might otherwise be unable to perform or able to perform only with considerably pain and discomfort.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A sedentary traction and support device for supporting the lumbosacral spine of a patient while the patient is in a sitting position on a seat or the like without preventing the patient from attaining on upright position while wearing the device, the device comprising:

a girdle having an upper edge and a lower edge and a back panel portion defined between first and second wrap panels wherein the wrap panels engage the sides and front of the patient and the back panel portion engages only the back of the patient, the wrap panels having an upper edge and a lower edge with at least the upper edge of the wrap panels converging toward the lower edges of the wrap panels; wherein the wrap panels, when fastened around a patient, position the upper edge at the girdle beneath the patient's scapulae and press on the patient's abdomen to provide supplemental support for the patient's spine;

rigid support mounting means on the back panel of the girdle in proximity with the upper edge and the lower edge thereof;

rigid vertical support means, having rigid horizontal bracking means extending therebetween at a location beneath the lower edge of the girdle, secured to the rigid support mounting means and extending downwardly from the mounting means for engagement with an upper surface of the seat upon which the patient is sitting so as to provide support for the patient's lumbosacral spine.

2. The traction and support device of claim 1 wherein the wrap panels having means for fastening comprising a hook and loop fabric.

3. The traction and support device of claim 1, wherein the girdle is made of a flexible pad-type material.

4. The traction and support device of claim 3, wherein the flexible pad-type material is latex.

5. The traction and support unit of claim 1, wherein the rigid vertical support means is a pair of vertical struts.

6. The traction and support unit of claim 5, wherein the mounting means includes a pair of pockets adjacent the upper edge of the girdle for receiving the ends of the vertical struts and sleeve means below pockets and engaging the vertical strut for stabilizing the frame with respect to the girdle.

7. The traction and support device of claim 6, wherein the vertical struts include adjustment means for extending the height thereof.

* * * * *

UNITED STATES PATENT AND TRADEMARK OFFICE
CERTIFICATE OF CORRECTION

PATENT NO. : 4,881,528

DATED : November 21, 1989

INVENTOR(S) : HENRY SCOTT

It is certified that error appears in the above-identified patent and that said Letters Patent is hereby corrected as shown below:

Column 4, claim 1, line 7:

reads "bracking means extending therebetween at a loca-"

should read -- bracing means extending therebetween at a loca- --

Signed and Sealed this

Eleventh Day of December, 1990

*Attest:*

HARRY F. MANBECK, JR.

*Attesting Officer*

*Commissioner of Patents and Trademarks*